United States Patent
Katoh et al.

(10) Patent No.: US 11,169,132 B2
(45) Date of Patent: Nov. 9, 2021

(54) MONITORING SYSTEM AND DETECTING DEVICE

(71) Applicants: OSAKA UNIVERSITY, Osaka (JP); ALLIED TELESIS HOLDINGS K.K., Tokyo (JP)

(72) Inventors: Noriyasu Katoh, Tokyo (JP); Minoru Aoki, Tokyo (JP); Eiichi Tamiya, Kyoto (JP)

(73) Assignees: OSAKA UNIVERSITY, Osaka (JP); ALLIED TELESIS HOLDINGS K.K., Tokyo (JP)

( * ) Notice: Subject to any disclaimer, the term of this patent is extended or adjusted under 35 U.S.C. 154(b) by 211 days.

(21) Appl. No.: 16/620,802

(22) PCT Filed: Jun. 6, 2018

(86) PCT No.: PCT/JP2018/021679
§ 371 (c)(1),
(2) Date: Dec. 9, 2019

(87) PCT Pub. No.: WO2018/225776
PCT Pub. Date: Dec. 13, 2018

(65) Prior Publication Data
US 2021/0278388 A1    Sep. 9, 2021

(30) Foreign Application Priority Data
Jun. 9, 2017    (JP) .............................. JP2017-114567

(51) Int. Cl.
*G01N 33/00* (2006.01)
*G01N 1/22* (2006.01)
(Continued)

(52) U.S. Cl.
CPC .......... *G01N 33/0073* (2013.01); *B01L 3/502* (2013.01); *G01N 1/2273* (2013.01);
(Continued)

(58) Field of Classification Search
CPC .. G01N 33/0073; G01N 27/48; G01N 1/2273; B01L 3/502; B01L 2300/02;
(Continued)

(56) References Cited

U.S. PATENT DOCUMENTS

| 2012/0122075 A1* | 5/2012 | Call | B01D 45/04 |
| | | | 435/3 |
| 2014/0260416 A1* | 9/2014 | McAlister | F25J 1/0236 |
| | | | 62/608 |

OTHER PUBLICATIONS

TEIKOKU SEN-I CO., Ltd., "Chemical agent detector-TEIKOKU SEN-I CO., Ltd.," [online], Sep. 2014, Internet <URL: http://www.teisen.co.jp/product/613/>.

* cited by examiner

*Primary Examiner* — Jennifer Wecker
*Assistant Examiner* — Jonathan Bortoli
(74) *Attorney, Agent, or Firm* — Concept IP LLP; Michael Zarrabian

(57) ABSTRACT

A purpose is to provide a monitoring system to monitor whether there is a substance to be monitored in the air, and a detecting device used in the monitoring system. The monitoring system includes a detecting device, an analyzing device, and an abnormality notification system. The detecting device determines whether the air is in an abnormal state on the basis of an output signal from an abnormality detection sensor, pours liquid to be inspected, into which the air is sucked and liquefied, into a previously-installed reagent container when determining the abnormal state, generates mixed liquid in which a reactant in the reagent container and the poured liquid to be inspected are mixed, and drops the generated mixed liquid to an electrode of the analyzing device. The analyzing device determines existence/non-existence of a substance to be monitored on the basis of the mixed liquid dropped to the electrode, and gives (Continued)

a predetermined notification to the abnormality notification system when determining that there is the substance to be monitored. The abnormality notification system gives a predetermined notification when receiving the notification from the analyzing device.

9 Claims, 12 Drawing Sheets

(51) Int. Cl.
    *G01N 27/48*     (2006.01)
    *B01L 3/00*     (2006.01)
    *G08B 21/12*     (2006.01)
    *G06K 9/00*     (2006.01)
    *G08B 5/22*     (2006.01)

(52) U.S. Cl.
    CPC ......... *G01N 27/48* (2013.01); *G06K 9/00771* (2013.01); *G08B 5/22* (2013.01); *G08B 21/12* (2013.01); *B01L 2200/10* (2013.01); *B01L 2200/16* (2013.01); *B01L 2300/02* (2013.01); *B01L 2300/0645* (2013.01)

(58) Field of Classification Search
    CPC ............. B01L 2200/10; B01L 2200/16; B01L 2300/0645; G08B 21/12; G08B 5/22; G06K 9/00771
    See application file for complete search history.

MONITORING SYSTEM AND DETECTING DEVICE

CROSS-REFERENCE TO RELATED APPLICATIONS

This application is a 35 U.S.C § 371 National Stage Entry of International Application No. PCT/JP2018/021679 filed Jun. 6, 2018, which claims the priority benefit of Japanese Patent Application No. JP2017-114567 filed Jun. 9, 2017, all of which are incorporated herein by reference in their entirety.

TECHNICAL FIELD

The present invention relates to a monitoring system to monitor whether there is a substance to be monitored in the air, and a detecting device used in the monitoring system.

BACKGROUND ART

As world affairs become turmoil, a risk of occurrence of terrorism or the like has been pointed out. Then, as a method of a terrorist act, a possibility of spraying of a chemical agent has been pointed out. Also, in addition to terrorism, there is a possibility that a harmful substance is released to the air by fire or an accident and influences a human body.

From such a situation, a chemical agent detector to detect a chemical agent in the air by an enzyme reaction has been known as described in Non Patent Literature 1 described in the following.

Also, a method of extracting an appropriate amount of liquid, in which a component in the air is dissolved in water, with a pipette or the like and mixing a medical agent that reacts with liquid to be inspected has been known in addition to the above-described chemical agent detector.

CITATION LIST

Non Patent Literature

Non Patent Literature 1: TEIKOKU SEN-I CO., Ltd., "Chemical agent detector-TEIKOKU SEN-I CO., Ltd.," [online], Internet <URL: http://www.teisen.co.jp/product/613/>

SUMMARY OF INVENTION

Technical Problem

Although it becomes possible to detect existence/non-existence of various kinds of chemical agents such as a nerve agent, a blister agent, a blood agent, and an asphyxiant by using various chemical agent detectors described in Non Patent Literature 1, it is not possible to do research unless the detectors are brought to a site. In that case, since an expert equipped with a special protective suit or the like needs to go to the site, there is danger to the expert.

Also, in a case of a method of mixing liquid to be inspected and a medical agent that reacts therewith by using a pipette or the like, handling by an expert is necessary and mixing operation needs to be performed in a laboratory. Thus, there is a problem that a measurement site is limited.

Solution to Problem

Thus, in view of the above problem, the present inventor invents a monitoring system, and a detecting device used in the monitoring system.

The first invention is a monitoring system to monitor whether there is a substance to be monitored in the air, the monitoring system including: a detecting device; an analyzing device; and an abnormality notification system, wherein the detecting device determines whether air is in an abnormal state on the basis of an output signal from an abnormality detection sensor, pours liquid to be inspected, into which the air is sucked and liquefied, into a previously-installed reagent container when detecting the abnormal state, generates mixed liquid in which a reactant in the reagent container and the poured liquid to be inspected are mixed, and drops the generated mixed liquid to an electrode of the analyzing device, the analyzing device determines existence/non-existence of the substance to be monitored on the basis of the mixed liquid dropped to the electrode, and gives a predetermined notification to the abnormality notification system when determining that there is the substance to be monitored, and the abnormality notification system gives a predetermined notification when receiving the notification from the analyzing device.

According to the present invention, in a case where it is determined by utilization of the abnormality detection sensor that the air is in an abnormal state, mixed liquid is generated by automatic pouring of liquid to be inspected, in which the air is liquefied, into the reagent container and mixing thereof with a reactant, and it is possible to automatically determine existence/non-existence of a substance to be monitored on the basis of that and to give a notification thereof. Accordingly, it is possible to safely and automatically determine existence/non-existence of a chemical agent, an agricultural chemical, a pesticide, or the like to be a substance to be monitored without an expert actually going to a site. Also, since it is only necessary to install a detecting device or the like, a measuring site is not limited.

In the above-described invention, the monitoring system may be configured in such a manner that the abnormality notification system acquires image information of an imaging device installed in a predetermined place and performs storing thereof in association with identification information of the imaging device, associates and stores identification information of an abnormality detection sensor and identification information of an imaging device that images a periphery of the abnormality detection sensor, and specifies identification information of a corresponding imaging device, when receiving the notification from the analyzing device, on the basis of identification information of an abnormality detection sensor in the notification and specifies image information of the imaging device.

In a case where it is notified that there is a substance to be monitored in the air, it is necessary to immediately check a periphery of the site. Thus, by utilization of the present invention, it is possible to immediately specify image information of the periphery of the site from image information imaged by the imaging device, and to perform a display thereof.

In the above-described invention, the monitoring system may be configured in such a manner that the abnormality notification system further stores day-and-time information in association with image information of the imaging device, specifies identification information of a corresponding imaging device, when receiving the notification from the analyzing device, on the basis of identification information of an abnormality detection sensor in the notification and specifies, based on the date and time information image information, of a predetermined prior time, from among the image information in the image capturing device.

When day-and-time information is associated with image information imaged by the imaging device in a manner of the present invention, it is possible to easily specify image information of a periphery of a site at a predetermined time before time of a notification indicating that there is a substance to be monitored. With this arrangement, it is possible to promptly find a suspicious person, for example.

In the above-described invention, the monitoring system may be configured in such a manner that the detecting device includes a control device, and a device unit including a roller unit, a liquefaction container, and a driving unit, the control device determines, when receiving an output signal from the abnormality detection sensor, whether the air is in an abnormal state on the basis of whether the output signal satisfies a predetermined condition, causes the liquefaction container, which stores liquid, to suck the air and causes the air to be dissolved and liquefied in the stored liquid when determining that the air is in the abnormal state, causes pouring of the liquefied liquid to be inspected into a reagent container installed in an installation unit in the roller unit, generates mixed liquid, in which the poured liquid to be inspected and the reactant are mixed, by causing a roller in the roller unit to rotate and to press the reagent container installed in the installation unit along with driving of the driving unit, and drops the generated mixed liquid to an electrode of the analyzing device.

According to the detecting device of the present invention, it is possible to automatically collect a mixed liquid to be analyzed in the analyzing device and to reduce a size.

In the above-described invention, the monitoring system may be configured in such a manner that a shaft of the driving unit and a shaft joined to an arm that supports the roller in the roller unit are interlocked through a band, and by a rotation of the shaft of the roller unit which rotation is caused through the band by a rotation of the shaft of the driving unit, the roller is rotated along an inclination surface of the installation unit through the arm and the reagent container is pressed toward the inclination surface.

In the above-described invention, the monitoring system may be configured in such a manner that at least one partition is provided in the reagent container, and liquid to be inspected and the reactant are mixed when the liquid to be inspected which is poured into the reagent container is pressed by a rotation of the roller and the partition is broken.

With these configurations of the invention, it is possible to automatically generate mixed liquid, in which a reactant in a reagent container and the reagent container are mixed, by installing the reagent container in a device unit in a detecting device and pouring liquid to be inspected thereto.

In the above-described invention, the monitoring system may be configured in such a manner that the partition is formed at an angle in a longitudinal direction of the reagent container.

A reactant is stored in a space separated by a partition in a reagent container. However, in a case where the partition is pressed by a roller, force applied to the partition is distributed and the partition becomes less likely to be broken when the partition is provided vertically with respect to a longitudinal direction of the reagent container. Also, there is a possibility that an outer wall of the reagent container is damaged in some cases. Thus, when a partition is formed at an angle in a longitudinal direction in a manner of the present invention, it is possible to concentrate force applied to the partition and to make it easier to break the partition.

Even with a configuration in a manner of the present invention, it is possible to automatically determine existence/non-existence of a substance to be monitored and to give a notification similarly to an invention in claim 1. That is, a monitoring system is a monitoring system to monitor whether there is a substance to be monitored in the air, the monitoring system including a detecting device and an analyzing device. The detecting device generates mixed liquid by mixing liquid to be inspected, into which the air is sucked and liquefied, with a reactant when determining that the air is in an abnormal state, and the analyzing device determines existence/non-existence of the substance to be monitored on the basis of the generated mixed liquid, and gives a predetermined notification when determining that there is the substance to be monitored.

According to the present invention, it is possible to safely and automatically determine existence/non-existence of a chemical agent, an agricultural chemical, or a pesticide to be a substance to be monitored without an expert actually going to a site. Also, since it is only necessary to install a detecting device or the like, a measuring site is not limited.

As a detecting device used in the monitoring system of the present invention, a configuration in a manner of the present invention is preferably included. That is, a detecting device is a detecting device used in a monitoring system to monitor whether there is a substance to be monitored in the air, the detecting device including a control device, and a device unit that includes a roller unit, a liquefaction container, and a driving unit. The control device determines, when receiving an output signal from the abnormality detection sensor, whether the air is in an abnormal state on the basis of whether the output signal satisfies a predetermined condition, causes the liquefaction container, which stores liquid, to suck the air and causes the air to be dissolved and liquefied in the stored liquid when determining that the air is in the abnormal state, causes pouring of the liquefied liquid to be inspected from the liquefaction container into a reagent container installed in an installation unit in the roller unit, generates mixed liquid, in which the poured liquid to be inspected and the reactant are mixed, by causing a roller in the roller unit to rotate and to press the reagent container installed in the installation unit along with driving of the driving unit, and causes, by dropping the generated mixed liquid to an electrode, the analyzing device that determines existence/non-existence of a substance to be monitored, which becomes an object to be monitored, on the basis of the generated mixed liquid.

Advantageous Effects of Invention

According to the present invention, in a case where it is determined that the air is in an abnormal state, it is possible to promptly detect this and to give a notification even in a case where there is no special knowledge. Also, it is possible to secure safety since automatic performance is possible without an expert going to a site.

DESCRIPTION OF EMBODIMENTS

Figure 1:
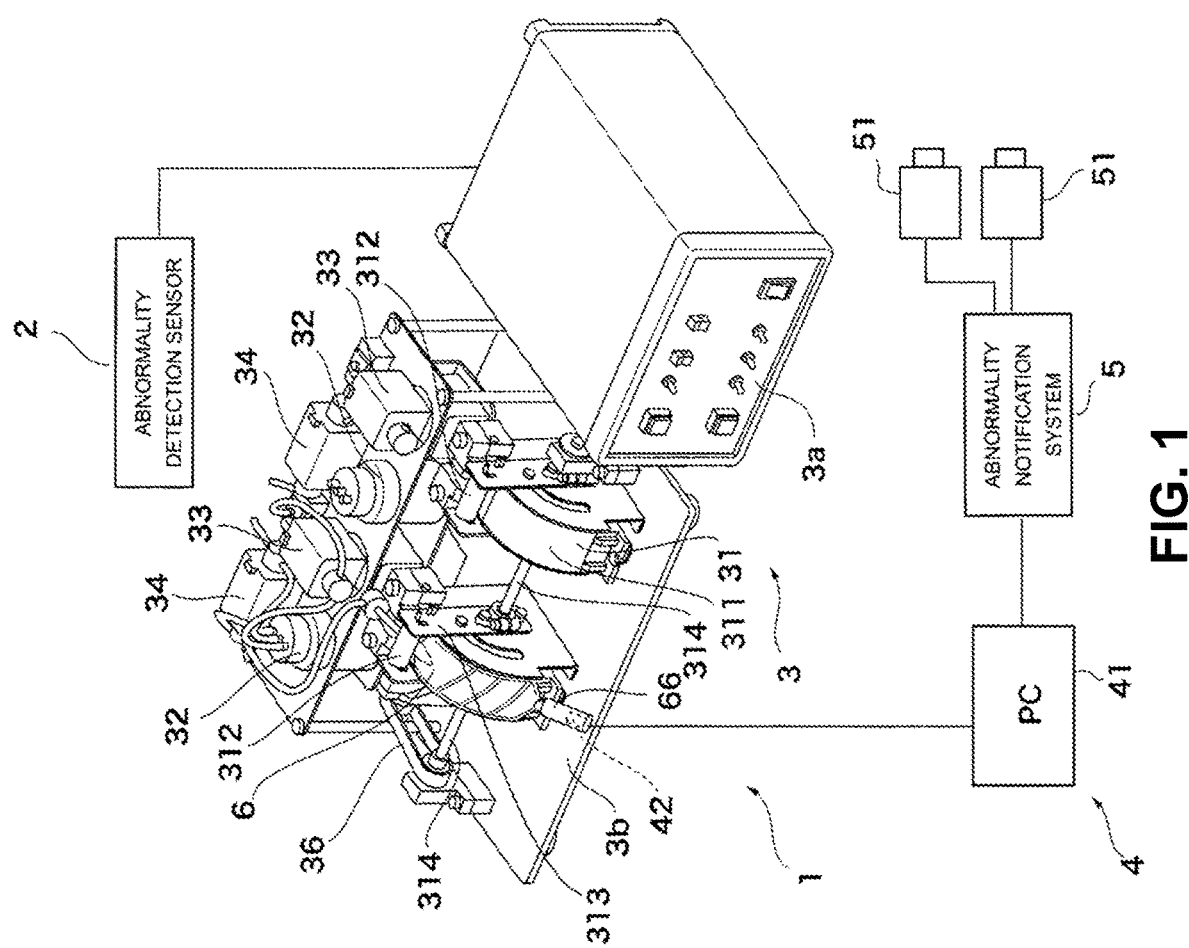
FIG. 1 is a view schematically illustrating an example of an appearance of a whole monitoring system of the present invention.
Figure 2:
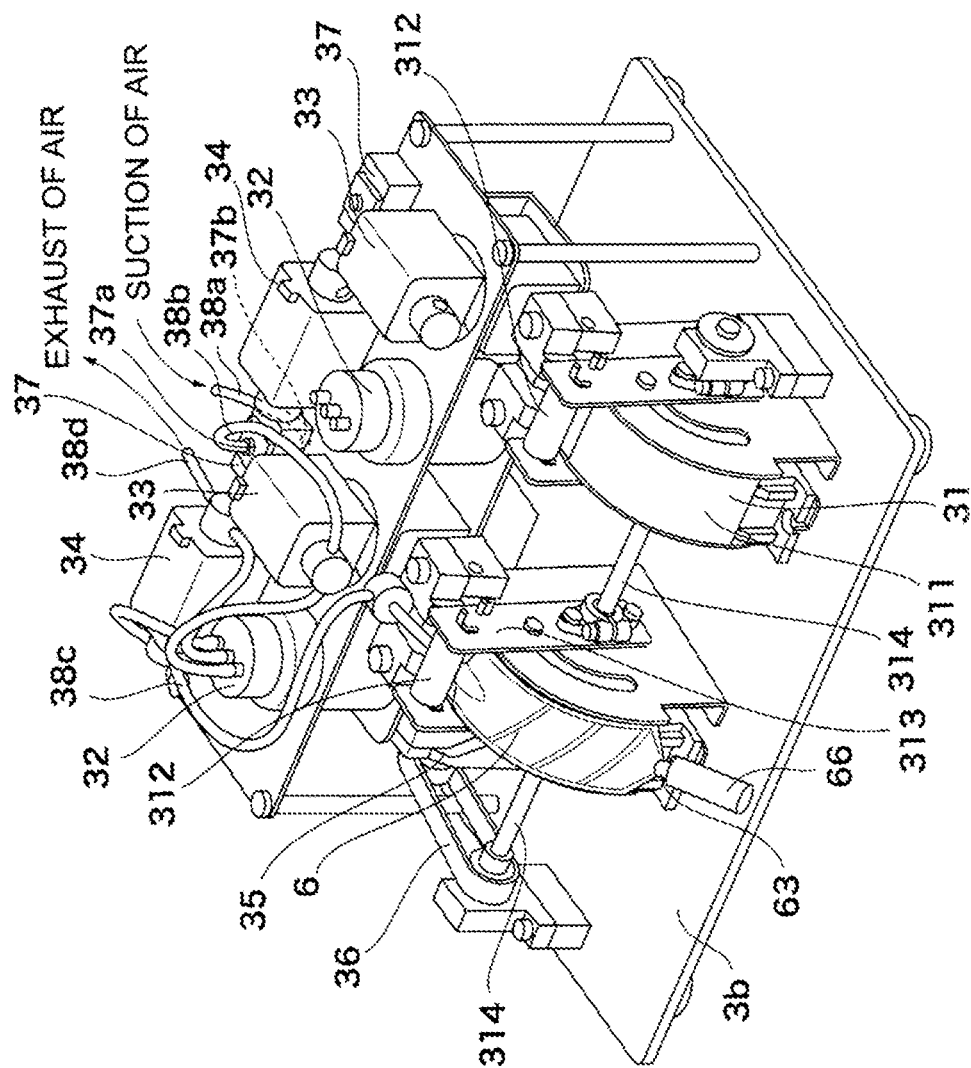
FIG. 2 is a view schematically illustrating an example of a device unit of a substance-to-be-monitored detecting device in the present invention.

An example of an appearance of a whole monitoring system 1 of the present invention is illustrated in FIG. 1. The monitoring system 1 of the present invention includes an abnormality detection sensor 2, a substance-to-be-monitored detecting device 3 (hereinafter, referred to as detecting device 3), an analyzing device 4, and an abnormality notification system 5.

The abnormality detection sensor 2 is a sensor to detect abnormality in the air, and is electrically connected to the substance-to-be-monitored detecting device 3 described later. The abnormality detection sensor 2 to detect abnormality in the air is preferably an abnormality detection sensor 2 that can perform relative value detection. In the relative value detection, abnormality in the air is detected according to an amount of a variation in a resistance value of the abnormality detection sensor 2 with a normal state of the air as a reference. For example, a semiconductor sensor "TGS2603" of Figaro Engineering Inc. can be used as the abnormality detection sensor 2. In the product, a metal-oxide semiconductor is formed as a gas sensing element on an alumina substrate. When there is gas to be detected, conductivity of an abnormality detection sensor 2 becomes high. An output signal corresponding to gas concentration is output according to a variation in the conductivity. Note that in addition to the above-described product, any abnormality detection sensor 2 may be employed as an abnormality detection sensor 2 as long as the abnormality detection sensor 2 is to achieve a goal of being used in determination whether to operate a detecting device 3.

On the basis of the output signal output from the abnormality detection sensor 2, the detecting device 3 operates in a case where this exceeds a predetermined threshold, sucks and liquefies the air, and pours the liquefied liquid to be inspected (pure water in which air is dissolved) into a predetermined reagent container 6. Then, while the reagent container 6 is pressed with a roller 312, the liquid to be inspected and a reactant in the reagent container 6 are mixed and the mixed liquid is dropped from the reagent container 6 to an electrode (printed electrode (carbon) 42) of the analyzing device 4 described later.

The detecting device 3 includes a control device 3a and a device unit 3b. The control device 3a and the device unit 3b are electrically connected, and each function of the device unit 3b works according to a control signal in the control device 3a. A programmable logic controller (PLC) can be used as the control device 3a. The control device 3a controls the device unit 3b according to a predetermined control program.

Note that the detecting device 3 starts operation on the basis of the output signal from the abnormality detection sensor 2. However, the above is not a limitation. By a different method, an abnormal state of the air may be detected and operation may be started.

The device unit 3b includes a roller unit 31, a liquefaction container 32, a pinch valve for an intake pump 33, a pinch valve for water-pouring/air exhaust 34, a driving unit (such as motor 35), a band 36, and an intake pump 37.

The roller unit 31 includes an installation unit 311 where the reagent container 6 is installed, the roller 312 that presses the reagent container 6 toward the installation unit 311, an arm 313 that supports the roller 312 and makes the roller 312 rotate along the installation unit 311, and a shaft 314 that joins the arm 313. A surface of the installation unit 311 is substantially arc-shaped, and the reagent container 6 is installed along an inclination surface of the installation unit 311. Then, the arm 313 rotates due to a rotation of the shaft 314, and the roller 312 rotates along the inclination surface of the installation unit 311. Also, the shaft 314 is interlocked with a motor shaft of a predetermined motor 35, which is attached to the device unit 3b, through the band 36. The shaft 314 rotates through the band 36 due to a rotation of the motor shaft of the motor 35.

Pure water to dissolve the air is stored in the liquefaction container 32. At least three tubes are attached to the liquefaction container 32. A first tube 38b delivers the air to the liquefaction container 32, and a second tube 38c pours liquid to be inspected into the reagent container 6 installed in the roller unit 31. A third tube 38d performs exhaust of when the air is liquefied.

It is preferable that the intake pump 37 operates constantly. An intake port 37b of the intake pump 37 and an intake tube 38a are connected, and the air around the abnormality detection sensor 2 is sucked through the intake tube 38a along with operation of the intake pump 37. Also, an exhaust port 37a of the intake pump 37 and the first tube 38b are connected, and the air sucked by the intake pump 37 is delivered to the liquefaction container 32 through the first tube 38b. Note that it is preferable that the abnormality detection sensor 2 and the intake tube 38a are in vicinity to each other. However, this is not a limitation. The intake tube 38a only needs to be in an effective range of the abnormality detection sensor 2. Also, the intake tube 38a and the first tube 38b may be separate tubes or may be one tube.

Each of the pinch valve for an intake pump 33 and the pinch valve for water-pouring/air exhaust 34 opens/closes a tube. The pinch valve for an intake pump 33 opens/closes the first tube 38b, and performs control of opening the first tube 38b in a case of delivering the air into the liquefaction container 32 and of closing the first tube 38b in other cases. The pinch valve for water-pouring/air exhaust 34 opens/closes the second tube 38c and the third tube 38d, and performs exhaust from the liquefaction container 32 by opening the third tube 38d in a case where the air is delivered to the liquefaction container 32 by the first tube 38b. Also, when liquefaction is performed, the third tube 38d is closed at certain timing such as a time point at which liquefaction is performed adequately. Then, the pinch valve for water-pouring/air exhaust 34 pours the liquid to be inspected from the liquefaction container 32 into the reagent container 6 by closing the third tube 38d and opening the second tube 38c. It is preferable that timing of opening the second tube 38c and timing of closing the third tube 38d is the same or substantially the same. That is, by a delivery of the air into the liquefaction container 32 by the first tube 38b, the air is sucked into the liquefaction container 32, and the sucked air is dissolved in pure water stored in the liquefaction container 32. On the one hand, since pressure in the liquefaction container 32 becomes high due to suction of the air into the liquefaction container 32, exhaust thereof is performed by the third tube 38d. On the one hand, in a case where a period in which the air can be adequately liquefied elapses, the third tube 38d is closed and the second tube 38c is opened while suction of the air by the first tube 38b is continued, whereby the liquid to be inspected in which the air is dissolved and which is stored in the liquefaction container 32 is poured from the liquefaction container 32 into the reagent container 6 through the second tube 38c. Then, at timing at which the pouring is ended, the first tube 38b is closed and the delivery of the air is ended. Note that in the present description, in the pinch valve for water-pouring/air exhaust 34, a configuration of integrally controlling opening/closing of two tubes that are the second tube 38c and the third tube 38d is described. However, a configuration in which control is performed by different pinch valves, that is, the second tube 38c is controlled by a pinch valve for water-pouring and the third tube 38d is controlled by a pinch valve for air exhaust may be employed.

Figure 3:
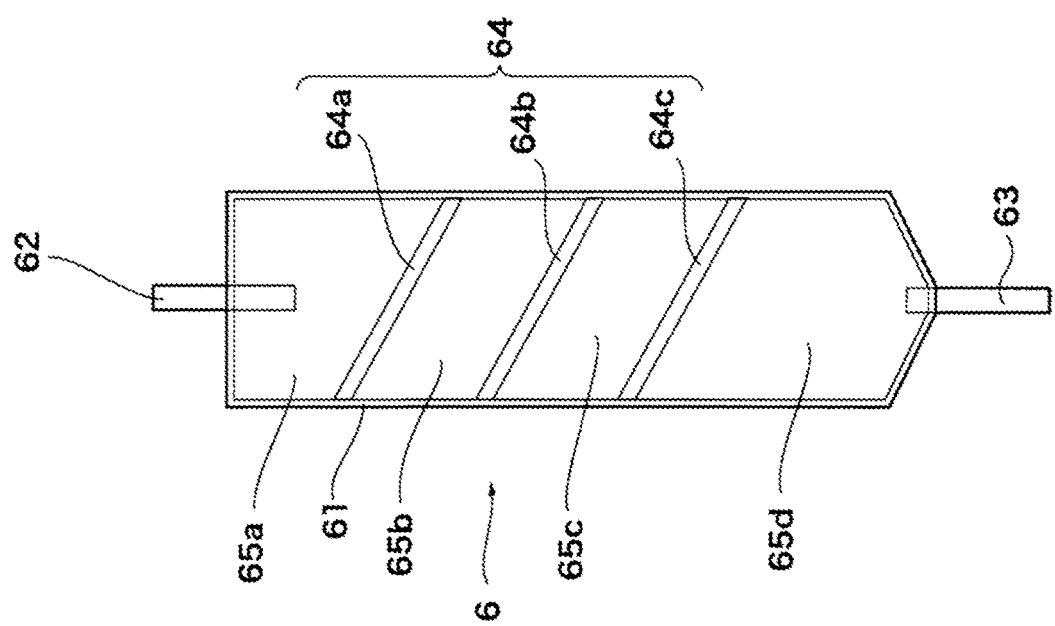
FIG. 3 is a view schematically illustrating an example of a reagent container used in the monitoring system of the present invention.

An enlarged view of the reagent container 6 is illustrated in FIG. 3. The reagent container 6 includes a bag-shaped outer wall 61, an inlet port 62 in an upper side of the outer wall 61 which port communicates with the second tube 38c and into which port liquid to be inspected is poured, an outlet port 63 that discharges mixed liquid in which the liquid to be inspected and a reactant in the reagent container 6 are mixed, and a storage part 66 that stores the mixed liquid discharged from the outlet port 63, the inside of the reagent container 6 being separated by a plurality of partitions 64. Since a case where two kinds of reactants are used is illustrated in FIG. 3, there are three partitions 64 (first partition 64a, second partition 64b, and third partition 64c), and the reagent container 6 is separated into four spaces (first space 65a, second space 65b, third space 65c, and fourth space 65d). Then, a first reactant is stored in the second space 65b formed by the first partition 64a and the second partition 64b, and a second reactant is stored in the third space 65c formed by the second partition 64b and the third partition 64c. For example, as reactants with respect to nerve gas, an enzyme (acetylcholinesterase) is stored as a first reactant in the second space 65b, and a substrate (acetylthiocholine) is stored as a second reactant in the third space 65c. In a case where these reactants are used, activity of acetylcholinesterase that is an enzyme is inhibited by a chemical agent, an organophosphate/carbamate-based agricultural chemical or pesticide, or the like. By utilization of this, the analyzing device 4 described later determines existence/non-existence of a chemical agent or the like. Thus, these reactants are effective for a case of determining existence/non-existence of an organophosphate-based chemical agent such as sarin or VX gas, an organophosphate/carbamate-based agricultural chemical or pesticide, or the like.

The reagent container 6 is installed on an inclination surface of the installation unit 311 of the roller 312. It is preferable that a longitudinal direction of the reagent container 6 and a rotating direction of the roller 312 are identical. In this case, the partitions 64 are formed at a predetermined angle in the longitudinal direction of the reagent container 6. In such a manner, since the partitions 64 are formed not in a vertical manner but at a predetermined angle with respect to the longitudinal direction, it becomes easier to break the partitions 64 with liquid inside when the roller 312 presses the reagent container 6.

A film having a polymer alloy is formed into a bag shape, whereby the outer wall 61 of the reagent container 6 is formed. For example, fusion of the outer wall 61 is performed by crimping by a sealer for about five seconds at around 250° C. Also, since the partitions 64 need to be formed in such a manner as to be easily broken compared to the outer wall 61, crimping is performed by a sealer for about one second at around 250° C. That is, the partitions 64 only need to be formed with intensity weaker than that of the outer wall 61. Note that a material of the reagent container 6 can be an arbitrary material and is not limited to the above.

The analyzing device 4 includes the printed electrode 42, to which mixed liquid in which liquid to be inspected and a reactant in the reagent container 6 are mixed is dropped, and electrically analyzes the mixed liquid dropped to the printed electrode 42 and determines existence/non-existence of a chemical agent to be monitored by using a computer 41. The printed electrode 42 is installed in an inner side of a storage part of the reagent container 6, and is configured to be soaked in the mixed liquid. As the analyzing device 4, a compact potentiostat "BDTminiSTAT100" and an analysis program thereof by BioDevice Technology, Ltd. can be used. A method of determining existence/non-existence of a chemical agent to be monitored according to the mixed liquid dropped to the printed electrode 42 can be realized by measuring of a degree of inhibition in activity of an enzyme by a publicly known method such as an electrochemical method by voltammetry.

That is, when a substrate is acetylthiocholine (ATCh), an enzyme is acetylcholinesterase (AChE), and a chemical agent to be monitored is nerve gas such as sarin, acetylthiocholine (ATCh) that is a substrate is metabolized by acetylcholinesterase (AChE) that is an enzyme, and thiocholine (TCh) is generated in the mixed liquid. Moreover, TCh is oxidized on the printed electrode 42 (carbon) and dithiobischoline is generated. Here, when there is a chemical agent to be monitored in the mixed liquid, the chemical agent is bonded to the enzyme (AChE) and inhibits metabolism of the substrate (ATCh). Here, it is possible to determine existence/non-existence of a chemical agent by analyzing, with the above-described compact potentiostat and analysis program thereof, a relationship between an applied voltage and detected current associated with an oxidation reaction on the printed electrode 42 (voltammetry).

When existence/non-existence of a chemical agent or the like to be monitored is determined by the analyzing device 4, information thereof is transmitted to the abnormality notification system 5 described later. That is, information indicating that a certain chemical agent is mixed in the air, identification information of an abnormality detection sensor 2, and day-and-time information are transmitted to the abnormality notification system 5.

The abnormality notification system 5 acquires image information (moving image information or still image information) of an imaging device 51 installed in a predetermined place such as a facility, or information from various abnormality detection sensors 2, and gives a notification to a predetermined screen or person in charge when it is received that there is abnormality. Also, the image information received from the imaging device 51 is stored in a predetermined storage device in association with day-and-time information, and identification information of the imaging device 51. Also, the abnormality notification system 5 associates and stores identification information of various abnormality detection sensors 2 and identification information of an imaging device 51 that images a periphery of the abnormality detection sensors 2.

For example, when information indicating that a chemical agent or the like is detected, and identification information of the abnormality detection sensor 2 are received from the analyzing device 4, the abnormality notification system 5 gives a notification thereof to a predetermined screen or a predetermined person in charge by an e-mail or a message. Along with this, on the basis of the identification information of the abnormality detection sensor 2 in the information received from the analyzing device 4, identification information of a corresponding imaging device 51 is specified, and image information imaged by the imaging device 51 is extracted from a storage device and displayed on a screen. Specifically, image information in a predetermined period such as ten minutes before day-and-time information at reception of the abnormality notification is extracted from the storage device and displayed on the screen. With this arrangement, it becomes possible to easily check image information before/after generation of abnormality.

Figure 12:
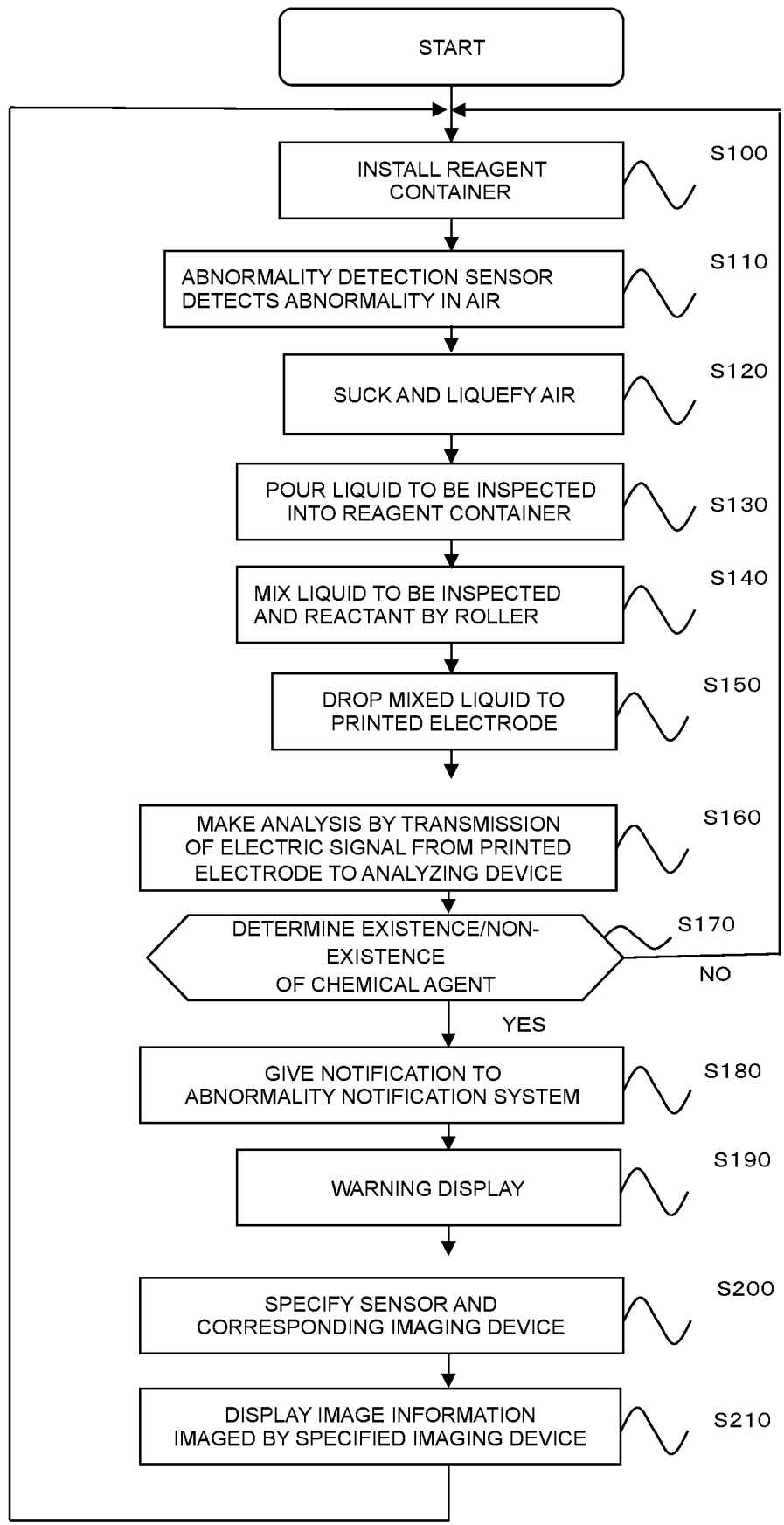
FIG. 12 is a flowchart illustrating an example of a processing process in the monitoring system of the present invention.

Next, an example of a processing process using the monitoring system 1 of the present invention will be described with reference to a flowchart in FIG. 12.

First, in the detecting device 3 of the monitoring system 1, the reagent container 6 including a reagent corresponding to a substance to be monitored is installed on an inclination surface of the installation unit 311 (S100). Then, the second tube 38c of the detecting device 3 is made to communicate with the inlet port 62 of the reagent container 6. Also, the printed electrode 42 of the analyzing device 4 is attached to an inner side of the storage part 66 provided at a leading end of the outlet port 63 of the reagent container 6.

Then, the monitoring system 1 is operated. The abnormality detection sensor 2 in the monitoring system 1 detects a state in the air and transits, to the control device 3a in the detecting device 3, an output signal indicating how much a resistance value of the abnormality detection sensor 2 varies with a normal state of the air as a reference. Then, in a case of determining that a variation in the resistance value of the abnormality detection sensor 2 exceeds a predetermined threshold, the control device 3a determines that abnormality of the air is detected and makes the detecting device 3 operate (S110).

That is, when determining that abnormality of the air is detected, the control device 3a of the detecting device 3 releases the pinch valve for an intake pump 33 and activates the intake pump 37, and the intake tube 38a sucks the air around the abnormality detection sensor 2 and takes the air into the intake pump 37 through the intake port 37b. Then, the air is delivered to the liquefaction container 32 from the first tube 38b that communicates with the exhaust port 37a of the intake pump 37, and processing of liquefaction is started (S120). Here, in the control device 3a, the pinch valve for water-pouring/air exhaust 34 releases the third tube 38d, and performs exhaust from the liquefaction container 32 by opening the third tube 38d in a case where the air is delivered by the first tube 38b.

Then, a period in which the air is adequately liquefied elapses, the control device 3a closes the third tube 38d and releases the second tube 38c with the pinch valve for water-pouring/air exhaust 34, and pours liquid to be inspected from the liquefaction container 32 into the reagent container 6 (S130). Then, when a certain amount of liquid to be inspected is poured, the control device 3a stops the intake pump 37, closes the first tube 38b with the pinch valve for an intake pump 33, and closes the second tube 38c with the pinch valve for water-pouring/air exhaust 34.

Then, when the liquid to be inspected is poured from the inlet port 62 of the reagent container 6 into the reagent container 6, the control device 3a starts mixing processing of the liquid to be inspected and a reactant by using the roller 312 (S140).

Figure 4:
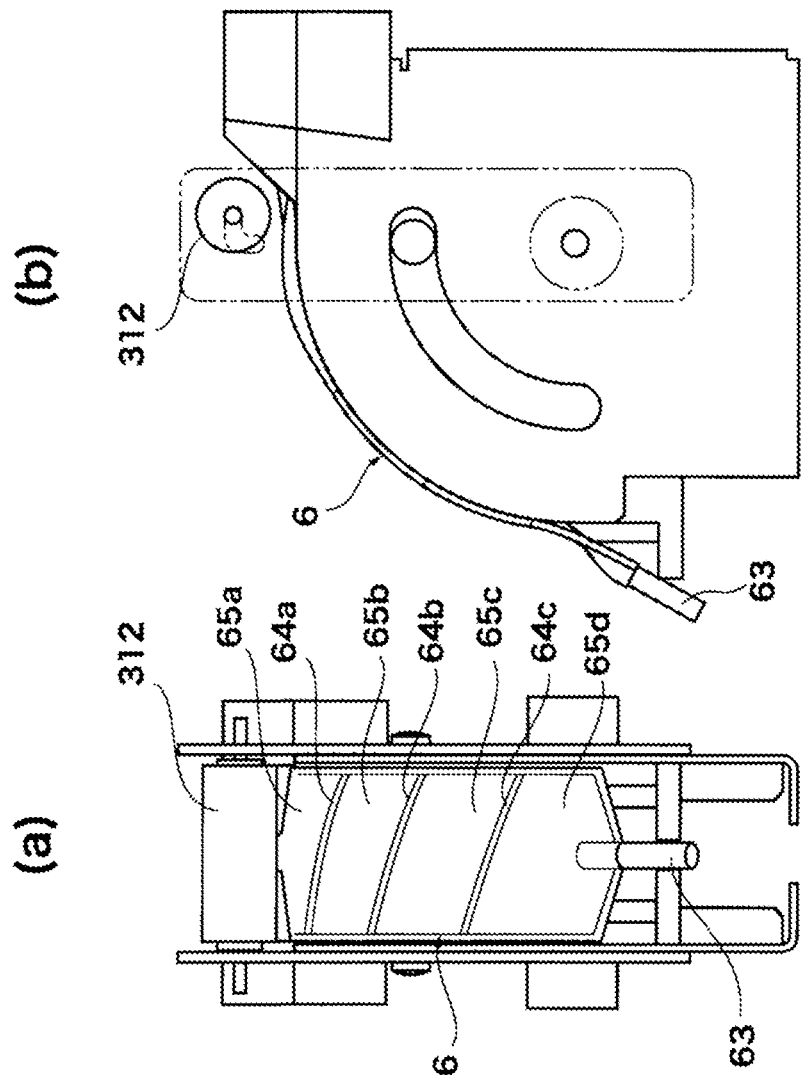
FIGS. 4(a) and 4(b) are views illustrating a state before a rotation of a roller.
Figure 5:
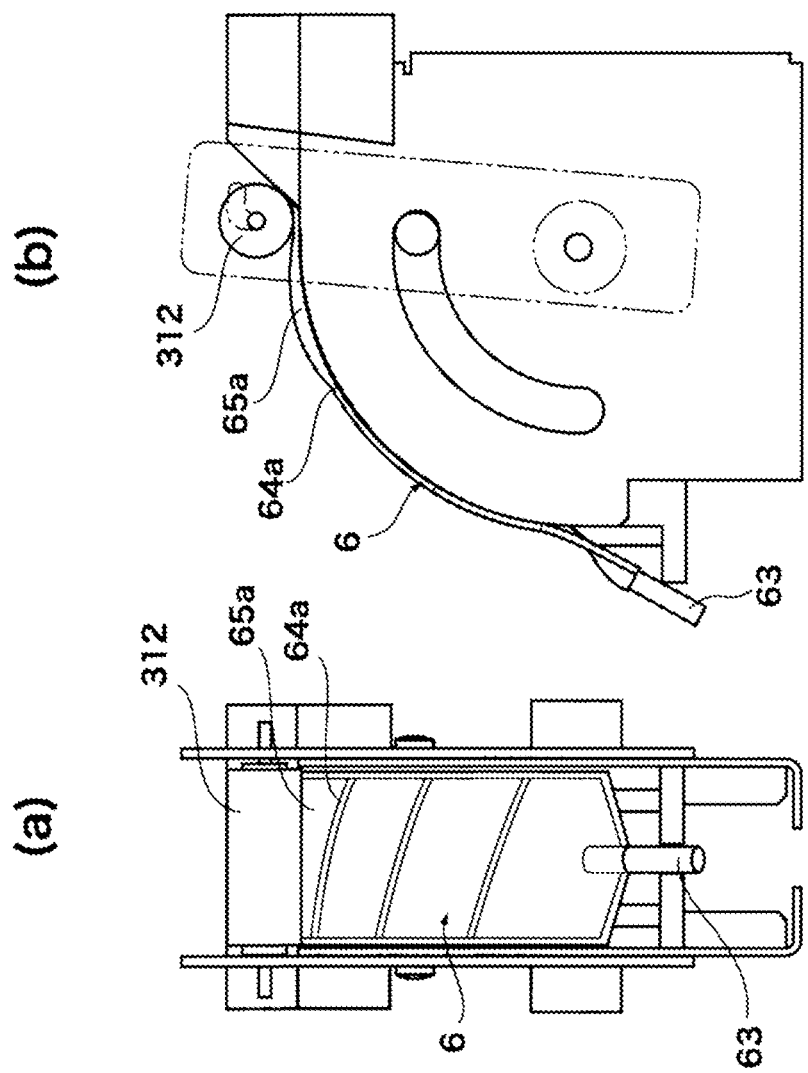
FIGS. 5(a) and 5(b) are views illustrating a state in which the roller rotates in a position in a first space.

First, the roller 312 is placed in the vicinity of the inlet port 62 of the reagent container 6 (FIGS. 4(a) and 4(b)), and the roller 312 starts a rotation from a side of the inlet port 62 toward a side of the outlet port 63 of the reagent container 6 when receiving control of starting mixing processing from the control device 3a. First, when the liquid to be inspected is poured from the inlet port 62 of the reagent container 6, the roller 312 starts a rotation to a lower side from the vicinity of the inlet port 62 and presses the reagent container in a direction of the inclination surface of the installation unit 311 after the liquid to be inspected is stored in the first space 65a (FIGS. 5(a) and 5(b)). Accordingly, the roller 312 starts rotating while pressing the reagent container 6 along the inclination surface of the installation unit 311. Then, since the roller 312 rotates while pressing the reagent container 6 from the vicinity of the inlet port 62 along the inclination surface of the installation unit 311, pressure is applied to the liquid to be inspected, which is stored in the first space 65a, and the first partition 64a is broken by the pressure. Then, the liquid to be inspected flows into the second space 65b.

Figure 6:
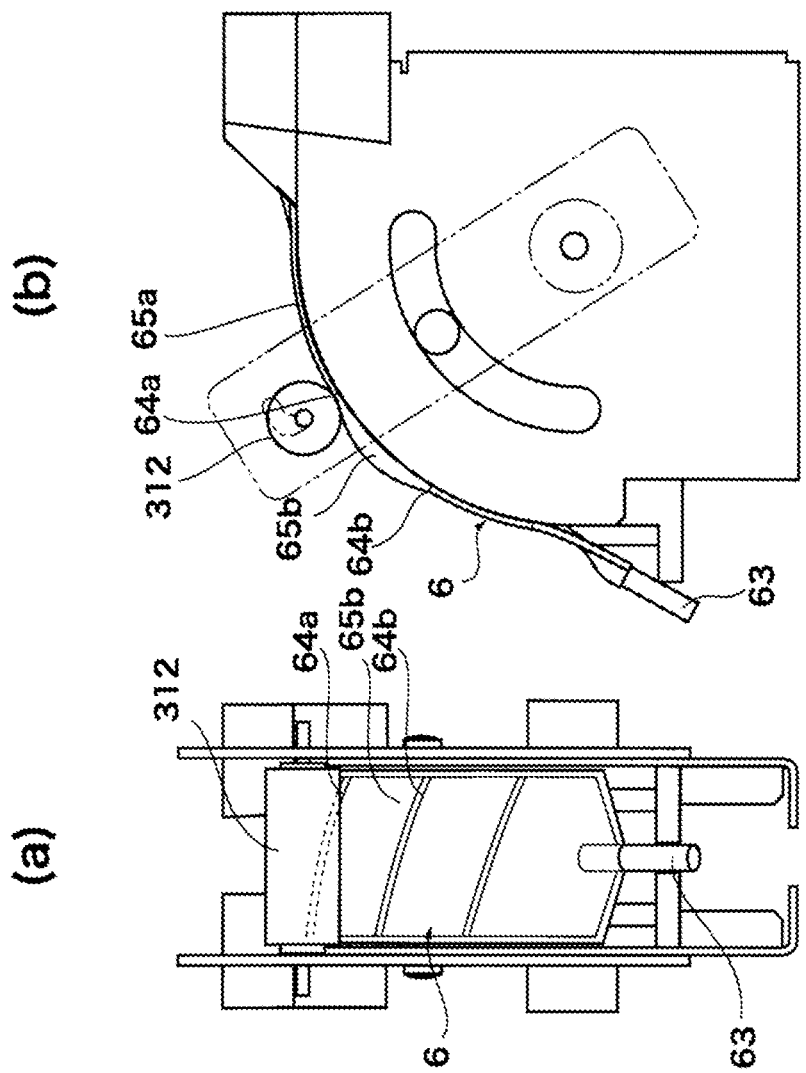
FIGS. 6(a) and 6(b) are views illustrating a state in which the roller stands by in a position on a first partition.
Figure 7:
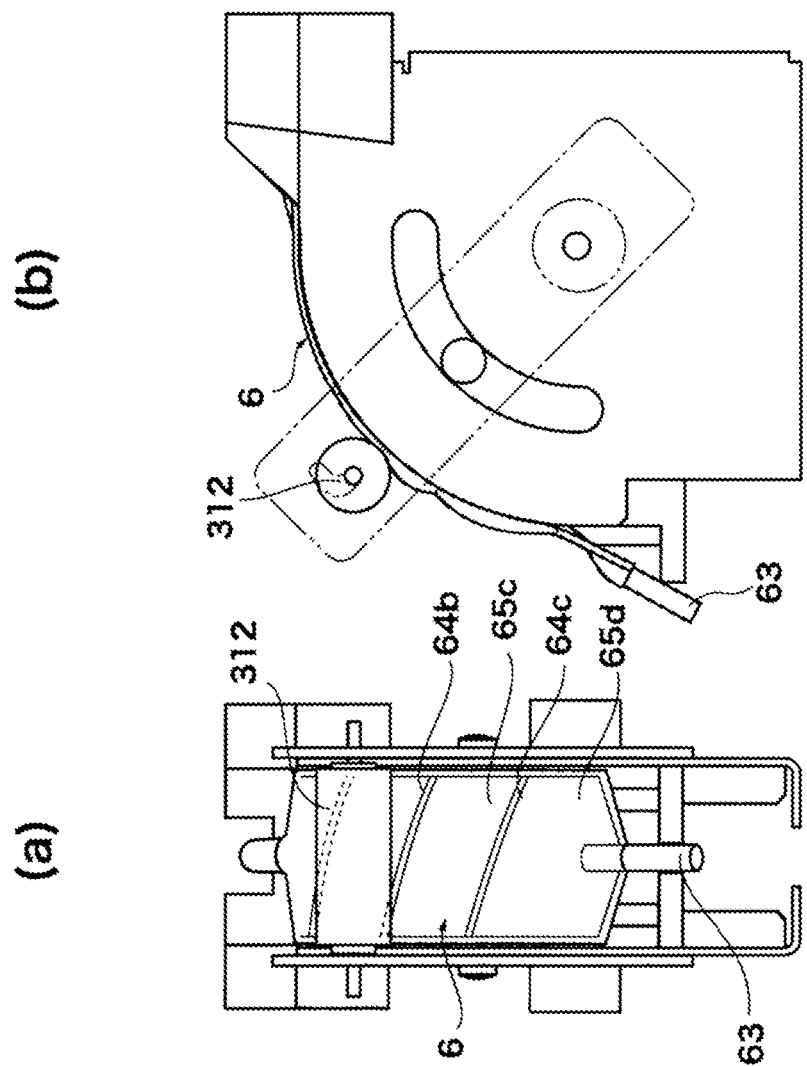
FIGS. 7(a) and 7(b) are views illustrating a state in which the roller rotates in a position in a second space.

When the liquid to be inspected flows into the second space 65b, the liquid to be inspected and a first reactant stored in the second space 65b are mixed. Then, in order to mix the liquid to be inspected and the first reactant, the control device 3a makes the roller 312 suspend the rotation and stand by in the vicinity of the first partition 64a for a predetermined period (FIGS. 6(a) and 6(b)). Then, after the predetermined period, the control device 3a makes the roller 312 rotate from an upper side of the second space 65b toward a lower side of the second space 65b (FIGS. 7(a) and 7(b)). Thus, pressure is applied to the mixed liquid and the second partition 64b is broken by the pressure. Then, when the second partition 64b is broken, the mixed liquid of the liquid to be inspected and the first reactant flows into the third space 65c.

Figure 8:
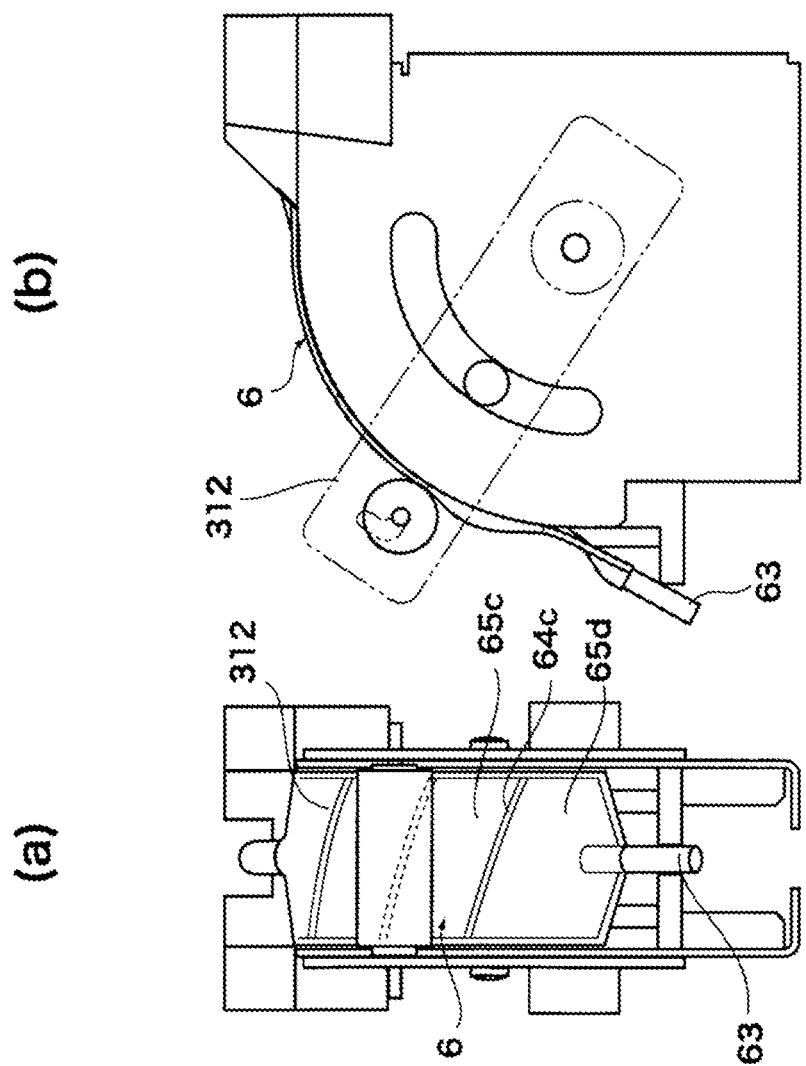
FIGS. 8(a) and 8(b) are views illustrating a state in which the roller stands by in a position on a second partition.
Figure 9:
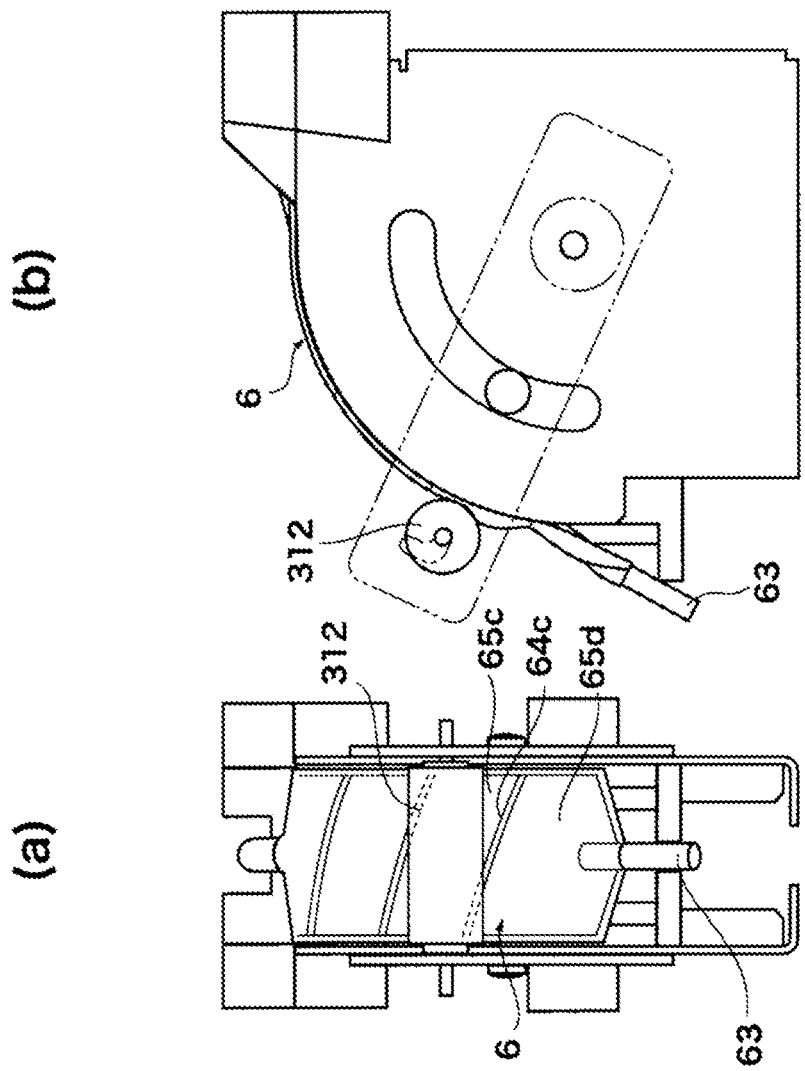
FIGS. 9(a) and 9(b) are views illustrating a state in which the roller rotates in a position in a third space.
Figure 10:
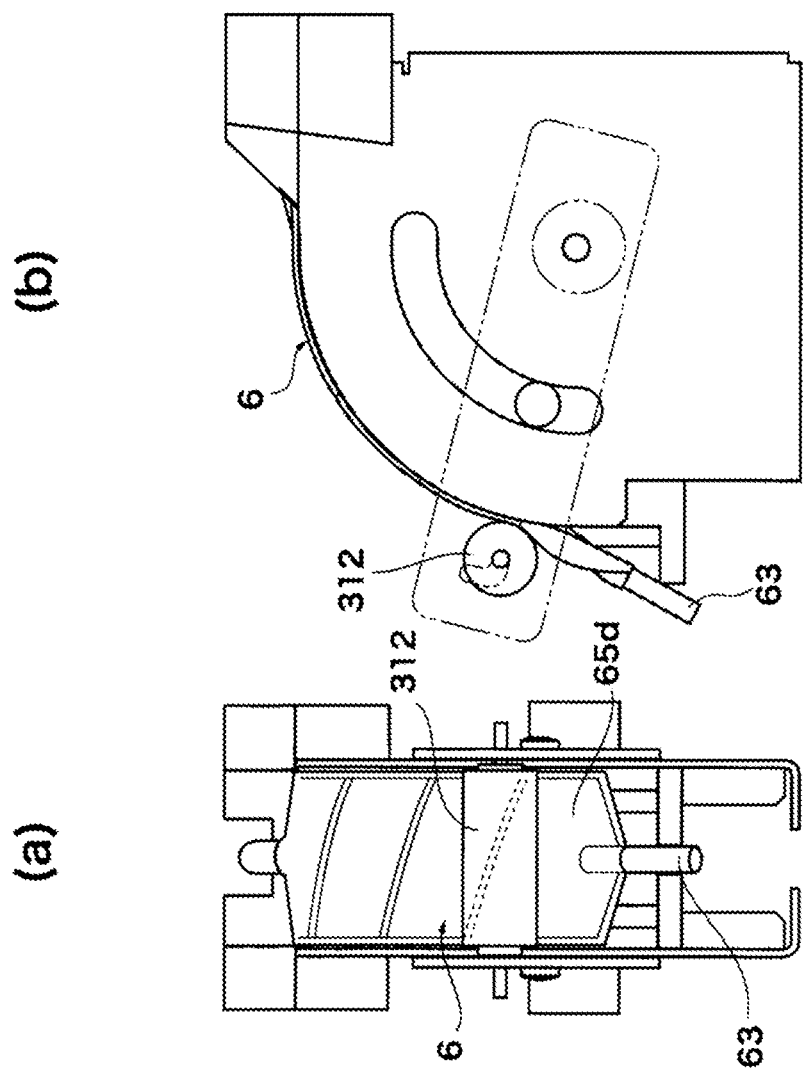
FIGS. 10(a) and 10(b) are views illustrating a state in which the roller rotates in a position on a third partition.
Figure 11:
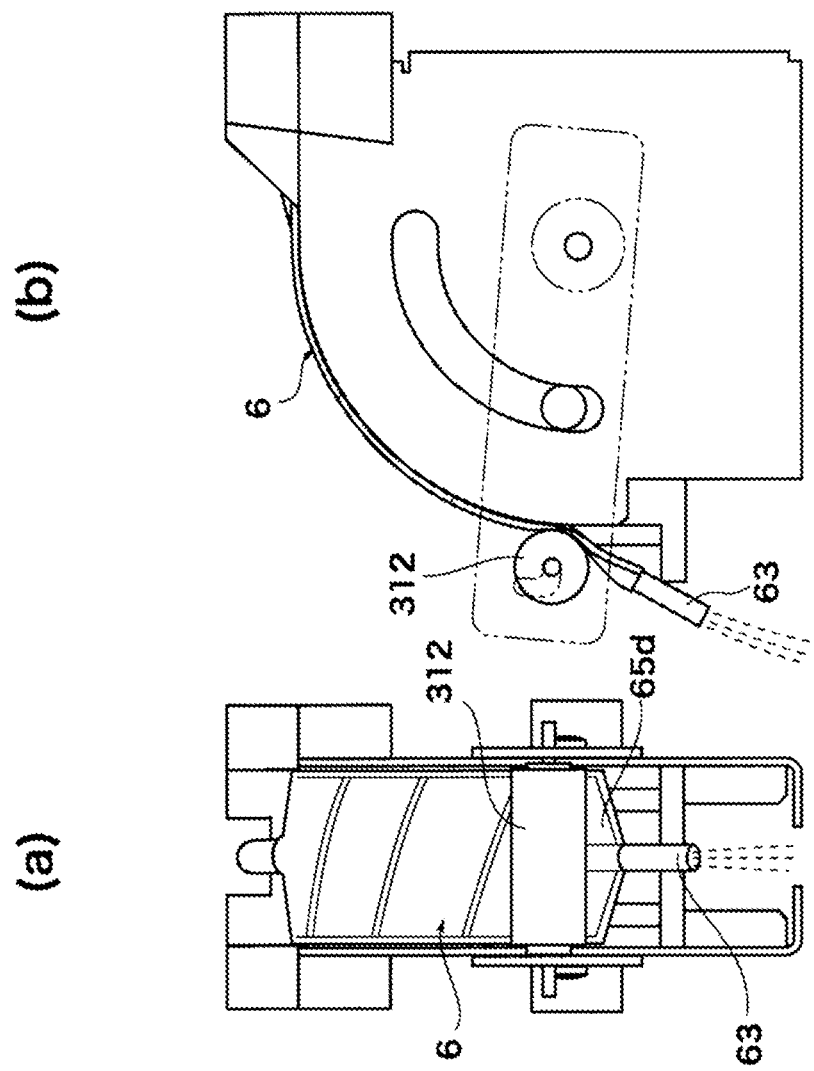
FIGS. 11(a) and 11(b) are views illustrating a state in which the roller stops in a position in a fourth space.

When the mixed liquid of the liquid to be inspected and the first reactant flows into the third space 65c, these and a second reactant stored in the third space 65c are mixed. Then, in order to mix the mixed liquid of the liquid to be inspected and the first reactant with the second reactant, the control device 3a makes the roller 312 suspend the rotation and stand by in the vicinity of the second partition 64b for a predetermined period (FIGS. 8(a) and 8(b)). Then, after the predetermined period, the control device 3a makes the roller 312 rotate from an upper side of the third space 65c toward a lower side of the third space 65c (FIGS. 9(a) and 9(b)). Thus, pressure is applied to liquid, in which these are mixed, and the third partition 64c is broken by the pressure. Then, the control device 3a makes the roller 312 keep rotating on the third partition 64c (FIGS. 10(a) and 10(b)). When the third partition 64c is broken, the mixed liquid of the liquid to be inspected, the first reactant, and the second reactant is discharged from the outlet port 63, and the mixed liquid is dropped to the printed electrode 42 provided inside the storage part 66 attached to the leading end of the outlet port 63 (S150). Then, the control device 3a makes the roller 312 ends the rotation in a predetermined stop position (FIGS. 11(a) and 11(b)). Note that setting of a period in which the control device 3a makes the roller 312 suspend and stand by in the vicinity of the first partition 64a, and in the vicinity of the second partition 64b can be arbitrarily changed according to a kind of a reactant. Also, periods of suspension may be different from each other.

When the mixed liquid is dropped to the printed electrode 42, the analyzing device 4 determines existence/non-existence of a chemical agent to be monitored by electrically analyzing the mixed liquid dropped to the printed electrode 42 (S160). That is, since an amount of metal microparticles collected to a vicinity of a surface of a working electrode corresponds to that of a substance to be monitored in the mixed liquid, the analyzing device 4 oxidizes the metal microparticles electrochemically, measures a current value generated in electrochemical deoxidization of the oxidized metal, and determines existence/non-existence or density of the substance to be monitored on the basis of the current value.

As a result, in a case where it is determined that there is no chemical agent to be a substance to be monitored (S170), a reagent container 6 is installed again along the inclination surface of the installation unit 311 in order to replace the reagent container 6 pressed by the rotation of the roller 312. On the one hand, in a case where it is determined that there is a chemical agent to be a substance to be monitored (S180), the analyzing device 4 notifies the abnormality notification system 5 of information indicating that the chemical agent is detected, identification information of the abnormality detection sensor 2, and day-and-time information (S180).

When the notification in S180 is received from the analyzing device 4, the abnormality notification system 5 displays a notification indicating that the chemical agent is detected on a predetermined screen and performs a warning display (S190). Also, a notification is given to a predetermined person in charge with an e-mail, a message, or the like. In the warning display in S190, the abnormality notification system 5 stores, in association with identification information of the abnormality detection sensor 2, information of a location thereof, and the information of a location of the abnormality detection sensor 2 is displayed in the warning display. For example, a warning display such as "a chemical agent is detected in a front entrance area" is preferably displayed.

Also, the abnormality notification system 5 specifies identification information of an imaging device 51 corresponding to the identification information of the abnormality detection sensor 2, and extracts image information imaged by the imaging device 51 in a predetermined period before the day-and-time information in S180 from a storage device and performs a display thereof on the basis of the identification information of the imaging device 51. With this arrangement, it is possible to promptly check a situation or the like in a periphery of the abnormality detection sensor 2 whether there is a person making a suspicious movement in the periphery of the abnormality detection sensor 2.

INDUSTRIAL APPLICABILITY

According to a monitoring system 1 of the present invention, in a case where it is determined that the air is in an abnormal state, it is possible to promptly detect this and to give a notification even in a case there is no special knowledge. Also, it is possible to secure safety since automatic performance is possible without an expert going to a site.

REFERENCE SIGNS LIST 1 monitoring system
2 abnormality detection sensor
3 detecting device
3a control device
3b device unit
4 analyzing device
5 abnormality notification system
6 reagent container
31 roller unit
32 liquefaction container
33 pinch valve for an intake pump
34 pinch valve for water-pouring/air exhaust
35 motor
36 band
37 intake pump
37a exhaust port
37b intake port
38a intake tube
38b first tube
38c second tube
38d third tube
41 computer of analyzing system
42 printed electrode
51 imaging device
61 outer wall
62 inlet port
63 outlet port
64 partition
64a to 64c first partition to third partition
65a to 65d first space to fourth space
66 storage part
311 installation unit
312 roller
313 arm
314 shaft

The invention claimed is:

1. A monitoring system to monitor whether there is a substance to be monitored in air, the monitoring system comprising:
a detecting device;
an analyzing device; and
an abnormality notification system,
wherein the detecting device
determines whether the air is in an abnormal state on the basis of an output signal from an abnormality detection sensor,
pours liquid to be inspected, into which the air is sucked and liquefied, into a previously-installed reagent container when determining the abnormal state,
generates mixed liquid in which a reactant in the reagent container and the poured liquid to be inspected are mixed, and
drops the generated mixed liquid to an electrode of the analyzing device,
the analyzing device
determines existence/non-existence of the substance to be monitored on the basis of the mixed liquid dropped to the electrode, and gives a predetermined notification to the abnormality notification system when determining that there is the substance to be monitored, and
the abnormality notification system
gives a predetermined notification when receiving the notification from the analyzing device.

2. The monitoring system according to claim 1, wherein the abnormality notification system
acquires image information of an imaging device installed in a predetermined place, and performs storing thereof in association with identification information of the imaging device, associates and stores identification information of an abnormality detection sensor and identification information of an imaging device that images a periphery of the abnormality detection sensor, and specifies identification information of a corresponding imaging device, when receiving the notification from the analyzing device, on the basis of identification information of an abnormality detection sensor in the notification, and specifies image information of the imaging device.

3. The monitoring system according to claim 2,
wherein the abnormality notification system
further stores day-and-time information in association with the image information of the imaging device, and
specifies identification information of a corresponding imaging device, when receiving the notification from the analyzing device, on the basis of the identification information of the abnormality detection sensor in the notification and specifies, based on the date and time information image information, of a predetermined prior time, from among the image information in the image capturing device.

4. The monitoring system according to claim 1,
wherein the detecting device
includes a control device, and a device unit including a roller unit, a liquefaction container, and a driving unit,
the control device
determines, when receiving the output signal from the abnormality detection sensor, whether the air is in an abnormal state on the basis of whether the output signal satisfies a predetermined condition,
causes the liquefaction container, which stores liquid, to suck the air and causes the air to be dissolved and liquefied in the stored liquid when determining that the air is in the abnormal state,
causes pouring of the liquefied liquid to be inspected into a reagent container installed in an installation unit in the roller unit,
generates mixed liquid, in which the poured liquid to be inspected and the reactant are mixed, by causing a roller in the roller unit to rotate and to press the reagent container installed in the installation unit along with driving of the driving unit, and
drops the generated mixed liquid to an electrode of the analyzing device.

5. The monitoring system according to claim 4,
wherein a shaft of the driving unit and a shaft joined to an arm that supports the roller in the roller unit are interlocked through a band, and
by a rotation of the shaft of the roller unit which rotation is caused through the band by a rotation of the shaft of the driving unit, the roller is rotated along an inclination surface of the installation unit through the arm and the reagent container is pressed toward the inclination surface.

6. The monitoring system according to claim 4,
wherein at least one partition is provided in the reagent container, and
the liquid to be inspected and the reactant are mixed when the liquid to be inspected which is poured into the reagent container is pressed by a rotation of the roller and the partition is broken.

7. The monitoring system according to claim 6,
wherein the partition is formed at an angle in a longitudinal direction of the reagent container.

8. A monitoring system to monitor whether there is a substance to be monitored in air, the monitoring system comprising:
a detecting device; and
an analyzing device,
wherein the detecting device
generates, when determining that the air is in an abnormal state, mixed liquid by mixing, with a reactant, liquid to be inspected into which the air is sucked and liquefied, and
the analyzing device
determines existence/non-existence of the substance to be monitored on the basis of the generated mixed liquid, and gives a predetermined notification when determining that there is the substance to be monitored.

9. A detecting device used in a monitoring system to monitor whether there is a substance to be monitored in air, the detecting device comprising:
a control device; and
a device unit that includes a roller unit, a liquefaction container, and a driving unit,
wherein the control device
determines, when receiving an output signal from an abnormality detection sensor, whether the air is in an abnormal state on the basis of whether the output signal satisfies a predetermined condition,
causes the liquefaction container, which stores liquid, to suck the air and causes the air to be dissolved and liquefied in the stored liquid when determining that the air is in the abnormal state,
causes pouring of the liquefied liquid to be inspected from the liquefaction container into a reagent container installed in an installation unit in the roller unit,
generates mixed liquid, in which the poured liquid to be inspected and the reactant are mixed, by causing a roller in the roller unit to rotate and to press the reagent container installed in the installation unit along with driving of the driving unit, and
causes an analyzing device, which determines existence/non-existence of a substance to be monitored which becomes an object to be monitored on the basis of the generated mixed liquid, to make an analysis by dropping the generated mixed liquid to a predetermined electrode.

* * * * *